(12) United States Patent
Garcia et al.

(10) Patent No.: US 7,626,074 B2
(45) Date of Patent: Dec. 1, 2009

(54) METHOD OF SCREENING CANDIDATE DRUGS FOR THE TREATMENT OF LEUKEMIA

(75) Inventors: Isidro Sanchez Garcia, Salamanca (ES); Jesus Perez Losada, Salamanca (ES)

(73) Assignees: Universidad de Salamanca, Salamanca (ES); Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 11/344,157

(22) Filed: Feb. 1, 2006

(65) Prior Publication Data

US 2006/0130168 A1    Jun. 15, 2006

Related U.S. Application Data

(62) Division of application No. 10/491,496, filed as application No. PCT/ES02/08520 on Nov. 11, 2002.

(30) Foreign Application Priority Data

Nov. 27, 2001  (ES)  ................. 200102630

(51) Int. Cl.
  *G01N 33/00*  (2006.01)
  *A01K 67/033*  (2006.01)
  *C12N 15/87*  (2006.01)

(52) U.S. Cl. ............... 800/3; 800/18; 435/455

(58) Field of Classification Search ............ None
  See application file for complete search history.

(56) References Cited

U.S. PATENT DOCUMENTS 5,491,283 A    2/1996   Groffen et al.

FOREIGN PATENT DOCUMENTS

WO    WO 01/02860    1/2001
WO    WO 02/059361    8/2002

OTHER PUBLICATIONS

Reichert et al Blood 2001; 97(5): 1399-403.*
Voncken et al. Cancer Res. 1992;52:4534-4539.*
Sigmund CD. Arterioscler Thromb Vasc Biol. 2000;20(6):1425-9.*
Kappel et al Current Opinions in Biotechnology ,1992, 548-553.*
Kolb et al, Gene, 1999, 227:21-31.*
Dyke et al, Cell, 108: 135-144, 2002.*
Bernardi et al Oncogene, 21: 3445-3458, 2002.*
Mullins et al Hypertension , 1993, 630-633.*
Wall RJ, Thenogenology, 1996, 45: 57-68.*
Neimann, H. Transgenic Res, 1998, 7: 73-75.*
Cobaleda et al Blood. 2000; 95(3):1007-13.*
Cameron et al., *Molecular Biotechnology*, 1997, 7:253-265.
Houdebine et al., *Transgenic Research*, 2000, 9:305-320.
Kolb et al., *Gene*, 1999, 227:21-31.
Miles et al., "Expression of the Ly-6#.1 (Sca-1). Transgene in adult hematopoietic stem cells and the developing mouse embryo," *Development*, 1991, vol. 127, pp. 537-547.
Honda et al., *Blood*, 1998, 91(6):2067-75.
Sanchez Garcia, "Chromosomal Abnormalities, Cancer and Mouse Models: The Critical Role of Translocation-Associated Genes in Human Cancer," *Current Genomics*, 2000, vol. 1, pp. 71-80.

\* cited by examiner

*Primary Examiner*—Deborah Krouch
*Assistant Examiner*—Anoop Singh
(74) *Attorney, Agent, or Firm*—Christopher T. McWhinney; Sullivan & Worcester LLP (57) ABSTRACT

Transgenic non-human mammals that reproduce human pathologies of stem cell origins, such as chromosomal anomalies associated with chronic myeloid leukemia, B-cell acute lymphoblastic leukemia, T-cell acute or lymphoblastic leukemia, or with the migration of hematopoietic or embryonic stem cells are provided. The transgenic non-human mammals can be produced using as a strategy the expression of genes involved in pathologies by a promoter that directs the expression of a transgene in Sca-1$^+$ cells. The transgenic animals constitute a model for the study of diseases and for the evaluation of compounds for the treatment and/or prevention of the diseases. DNA construct and methods useful for producing the non-human transgenic mammals are also provided.

4 Claims, 6 Drawing Sheets

FIG. 2B
LIVER

FIG. 3C ated is a stem cell [Blood (2000), 95:1007-1113; Oncogene (2000) 19(20): 2413-2422; Nature (2001) 414; 105-111].

METHOD OF SCREENING CANDIDATE DRUGS FOR THE TREATMENT OF LEUKEMIA

This application is a DIV of application Ser. No. 10/491,496, filed Apr. 1, 2004, which is a 371 of PCT/ES02/08520, filed Nov. 11, 2002, which claims priority to application filed in Spain P200102630, filed on Nov. 27, 2001.

FIELD OF THE INVENTION

The invention relates to transgenic non-human mammals that reproduce human pathologies of stem cell origins using, as a strategy, expression of genes involved in said pathologies in human beings by means of a promoter that directs expression of a transgene in Sca-1 cells.

BACKGROUND OF THE INVENTION

Transgenic animals are animals that carry an exogenous gene (transgene) in their genome, said gene having been introduced into germ cells of the animal, or into a predecessor thereof, at an early stage of development. The introduction of a transgene into the animal may have the aim of studying the behavior, expression or function of the gene introduced. Alternatively, the aim could be to genetically improve the affected individual for therapeutic ends or to improve the animal.

The generation of transgenic mammals is well established (see for example, Hogan, Constantini & Lacy (1986), "Manipulating the Mouse Embryo. A Laboratory Manual", Cold Spring Harbor Laboratory, Cold Spring Harbor (1986)) and proof of this is the high number of articles and patents that describe transgenic mammals. By way of illustration, the U.S. Pat. Nos. 4,736,866, 4,873,191, 5,175,383 and 5,175,384 can be cited.

The expression of a transgene can confer a new phenotype on the mammal. Depending on the transgene inserted and its level of expression in the mammal, the animal can be made to be more or less susceptible to a given disease. Such transgenic mammals are valuable models for the in vivo study of compounds that could potentially be useful in the treatment or prevention of said disease, and/or in the development of useful methods for the diagnosis of said disease.

The term "human pathology of stem cell origin" includes a group of human diseases, both neoplastic and non-neoplastic, that are of both hematopoietic and non-hematopoietic stem cell origin, for example, myeloid leukemias, B-cell lymphoid leukemias, T-cell lymphoid leukemias, lymphomas, sarcomas and pathologies of stem cell development, for example, congenital immunodeficiency, and Fanconi anemia, etc. Malignant neoplastic pathology (which is almost entirely of stem cell origin) is currently treated in human beings by a combination of strategies of chemotherapy, radiotherapy and/or surgery; strategies that do not discriminate between normal cells and tumor cells. Therapeutic treatment of non-neoplastic pathology is performed by substitutive therapies (immunoglobulins, vaccines, transfusions, etc.).

In recent years, activated genes and/or genes generated by chromosomal anomalies associated with both hematopoietic tumors and solid tumors have been identified [Annu. Rev. Genetics (1997) 31: 429-453]. Despite being identified, there are currently no animal models that reproduce said pathology [Oncogene (1999) 18: 5248; Oncogene (1999) 18: 5249-5252], though it has been shown that said genes are tumorigenic in vivo [Current Genomics (2000), 1:71-80]. Similarly, recently it has been shown that the target where the cancer is initiated is a stem cell [Blood (2000), 95:1007-1113; Oncogene (2000) 19(20): 2413-2422; Nature (2001) 414; 105-111].

In Current Genomics (2000), 1:71-80, some known mouse models are mentioned that express genes or gene fusions that are activated by chromosomal anomalies associated with different pathologies, for example, chronic myeloid leukemia (BCR-ABL$^{p210}$); B-cell acute lymphoblastic leukemia (BCR-ABL$^{p190}$), B-cell acute lymphoblastic leukemia (HOX11, RHOM2/LMO-2 and TAL1), etc. However, said models have only shown that the proteins expressed by said genes or gene fusions are tumorigenic, but they have not specifically reproduced the human pathology with which they are associated.

In view of the devastating effects of human pathologies of stem cell origin, there is a need to develop appropriate animals that provide an in vivo model for studying said human pathology as well as potentially useful compounds in the treatment and/or prevention of said pathology.

SUMMARY OF THE INVENTION

The invention tackles the problem of developing animal models that reproduce human pathology of stem cell origin.

The solution provided by the invention is based on the discovery that transgenic mice that contain a DNA construct that comprises a gene that is created and/or activated by chromosomal anomalies associated with different types of leukemia, or by hematopoietic or embryonic stem cell migration, said gene being controlled by a promoter that directs the expression of said gene in Sca-1$^+$ cells, such as stem cells, develop variable levels of human pathology, both neoplastic and non-neoplastic, of hematopoietic or non hematopoietic stem cell origin. By directing the expression of the different genes to the behavior of stem cells by means of the use of a promoter that directs the expression of such genes in Sca-1$^+$ cells, it has been possible to generate a set of animal models that reproduce the human pathology. This fact has been shown by means of the generation of a set of transgenic mice that possess genotypes that confer a greater tendency to develop the human pathology of stem cell origin when compared to non-transgenic mice. The transgenic mammals provided by this invention constitute, therefore, a new and useful model for the study of said diseases and for the evaluation of useful compounds for the treatment and/or prevention of said diseases.

The animal models that reproduce the human pathology of stem cell origin provided by this invention allow: a) use of a unique tool for studying how such a pathology is generated and maintained and how it develops; b) prediction of the efficacy of potentially valid therapies for human beings; c) discovery of new therapies; and d) genomic identification of alleles that suppress or increase the natural course of each pathology.

Therefore, an object of this invention is a DNA construct that comprises a gene that is created and/or activated by a chromosomal anomaly associated with a human pathology of stem cell origin, said gene being controlled by a promoter that directs the expression of said gene in Sca-1$^+$ cells.

An additional object of this invention is a transgenic non-human mammal that has a genotype that confers a greater tendency to develop the human pathology of stem cell origin when compared to a non-transgenic mammal. Said transgenic non-human mammal is useful for, among other things, studying said pathology and evaluated potentially useful compounds for treating and/or preventing said pathology. Therefore, an object of this invention constitutes a transgenic non-human mammal that contains a transgene and its progeny.

An additional object of this invention is a transgenic mouse that contains a transgene and its progeny. In a particular embodiment, said transgenic mouse is selected from the group made up of Sca-1+ BCR-ABL$^{p210}$, Sca-1+ BCR-ABL$^{p190}$, Sca-1+ Slug, Sca-1+ Snail, Sca-1+ HOX11, Sca-1+ RHOM2/LMO-2, Sca-1+ TAL1.

Another additional object of this invention is a procedure for the preparation of a transgenic non-human mammal useful as an animal model for in vivo study of human pathology of stem cell origin.

Another additional object of this invention is a cell line of transgenic non-human mammals that contains said DNA construct in its genome.

Another additional object of this invention is the use of a promoter that directs the expression of a gene in Sca-1+ cells for the generation of animal models that reproduce human pathology of stem cell origin.

Another additional object of this invention is the use of said transgenic non-human mammal in the evaluation of potentially useful compounds for the treatment and/or prevention of human pathology of stem cell origin.

Another additional object of this invention is the use of a promoter that directs the expression of a gene in Sca-1+ cells as a vehicle of therapeutic strategies. Pharmaceutical compositions that contain a DNA construct that comprises said promoter and a therapeutic gene, as well as the use of said promoter that directs the expression of a gene in Sca-1+ cells constitute additional objects of this invention.

Other objects will become apparent for one skilled in the art on seeing the description and claims.

BRIEF DESCRIPTION OF THE FIGURES

FIG. 1 consists of a set of plots and photographs that constitute the phenotype and histological demonstration of Sca-1+ BCR-ABL$^{p210}$ mice with chronic myeloid leukemia.

FIG. 1C shows a representative staining of the peripheral blood of Sca-1+ BCR-ABLP$^{210}$ mice in blast crisis stained with Giemsa where the blast cells can be seen.

FIG. 3 consists of a set of plots and photographs that constitute the phenotype and histological demonstration of myeloid and lymphoid blast crisis in Sca-1+ BCR-ABL$^{p190}$ mice with B-cell acute lymphoblastic leukemia.

DETAILED DESCRIPTION OF THE INVENTION

The invention provides a DNA construct, hereinafter the DNA of the invention, that comprises a gene that is created and/or activated by a chromosomal anomaly associated with a human pathology of stem cell origin, said gene being under the control of a promoter that directs the expression of said gene in Sca-1+ cells. In a particular embodiment, said chromosomal anomaly associated with a human pathology of stem cell origin is selected from among the chromosomal anomalies associated with chronic myeloid leukemia, B-cell acute lymphoblastic leukemia, T-cell acute lymphoblastic leukemia, or with the migration of hematopoietic or embryonic stem calls. Alterations of the c-kit receptor or its ligand, the stem cell factor (SCF), are an example of human pathology associated with migration of hematopoietic or embryonic stem cells.

As used in this description, the expression "gene that is created and/or activated by a chromosomal anomaly associated with a human pathology of stem cell origin", hereinafter, the activatable gene, refers to a gene or gene fusion that, when incorporated into the genome of a mammal, increases the probability that said mammal develops the pathology with which said gene or gene fusion is associated. In a particular embodiment, said activatable gene is a gene that is created and/or activated by chromosomal anomaly associated with a human pathology of stem cell origin selected from the chromosomal anomalies associated with chronic myeloid leukemia, B-cell acute lymphoblastic leukemia, T-cell acute lymphoblastic leukemia, or with hematopoietic or embryonic stem cell migration. By way of illustration, said activatable gene is selected from among the genes identified as BCR-ABL$^{P210}$, BCR-ABL$^{P190}$, Slug, Snail, HOX11, RHOM2/LMO-2 and TAL1. More specifically, in a particular embodiment, said activatable gene is selected from the following genes:

Human gene fusion BCR-ABL$^{P210}$ which is produced as a result of the t(9;22)(q34;q11) and which is associated with chronic myeloid leukemia; the patients who present this chromosomal anomaly develop a blast crisis over time, which is an evolutionary phenomenon characteristic of said disease;

Human BCR-ABL$^{P190}$, an oncogene generated by t(9;22) chromosomal translocation and associated with B-cell acute lymphoblastic leukemia;

Murine Slug, a gene that participates in the mobilisation of hematopoietic stem cells;

Murine Snail, a gene of the Slug family that participates in the embryonic stem cell migration;

Human HOX11, a gene activated by chromosomal anomalies associated with T-cell acute lymphoblastic leukemia;

Human RHOM2/LMO-2, a gene activated by chromosomal anomalies associated with T-cell acute lymphoblastic leukemia; and Murine TAL1, a gene activated by chromosomal anomalies associated with T-cell acute lymphoblastic leukemia.

The activatable genes identified as BCR-ABL$^{P210}$, BCR-ABL$^{P190}$, HOX11, RHOM2/LMO-2 and TAL1 are described in Annu. Rev. Genet. (1997) 31: 429-453. The Slug gene has been described by Nieto M A, Sargent M G, Wilkinson D G and Cooke J (1994) "Control of cell behavior during vertebrate development by Slug, a zinc-finger gene" Science 264: 835-849; and the Snail gene has been described by Jiang R, Lan Y, Norton C R, Sundberg J P and Gridley T (1998) "The Slug gene is not essential for mesoderm or neural crest development in mice" Developmental Biology 198:277-285; Sefton M, Sanchez S and Nieto M A (1998) "Conserved and divergent roles for members of the Snail family of transcription factors in the chick and mouse embryo" Development 125-3111-3121; and Hemavathy K, Asthraf S I and Lp Y T (2000) "Snail/Slug family of repressors: slowly going into the fast lane of development and cancer". Gene 257:1-12. These activatable genes can be obtained from the information provided by the aforementioned publications. Although they have been particularized for several particular embodiments, the teachings of the present invention can be applied to any gene or gene fusion created and/or activated by a chromosomal anomaly present in the cancer. Information related with such genes or gene fusions can be found, for example, in Annu. Rev. Genet. (1997) 31; 429-453.

The promoter that directs expression of the activatable gene in Sca-1$^+$ cells is a sequence of nucleic acids implicated and necessary in the initiation of transcription, which directs the expression of the activatable gene in Sca-1$^+$ cells, and includes the binding site of RNA polymerase. Within the context of the present invention, the term "promoter" may include other sites to which the transcription regulating proteins can bind. In a particular embodiment, the promoter that directs the expression of the activatable genes in Sca-1$^+$ cells is the pLy-6E1 promoter of mouse or a functional fragment thereof, in other words, it is able to direct the tissue specific expression of the different transgenes in mice. The pLy-6E1 promoter is well characterised and contains all the elements necessary for the selective expression in Sca-1$^+$ cells [Miles C., Sanchez M-J, Sinclair A, and Dzierzak, E. (1997) "Expression of the Ly-6E.1 (Sca-1) transgene in adult hematopoietic stem cells and the developing mouse embryo". Development 124:537, 547].

The expression "operatively bound" relates to the orientation of the promoter with respect to sequence of activatable gene. The promoter is placed such that it is able to control or regulate the expression of said activatable gene.

The DNA construct of the invention can be easily obtained by conventional digestion methods with restriction and binding enzymes, and similar enzymes as described by Sambrook, Fitsch and Maniatis, eds., (1989) "Molecular Cloning: A Laboratory Manual". Cold Spring Harbor Laboratory Press, Cold Spring Harbor N.Y.

The DNA construct of the invention can be used, if desired, for the production of vectors useful for transforming mammal embryos and for generating transgenic animals using conventional methods such as those described by Sambrook et al., cited above.

Alternatively, the DNA construct of the invention can be used for obtaining a linear fragment of DNA useful for microinjection of DNA into fertilized oocytes in order to generate transgenic animals. Said linear fragment of DNA useful for microinjection can be obtained by means of cutting with restriction enzymes in order to obtain a linear DNA fragment that comprises the activatable gene.

In another aspect, the invention provides a transgenic non-human mammal that contains on its genome a DNA construct of the invention, in other words, a construct that comprises a gene that is created and/or activated by an anomalous chromosome associated with a human pathology of stem cell origin, for example, chromosomal anomalies associated with chronic myeloid leukemia, B-cell acute lymphoblastic leukemia, T-cell acute lymphoblastic leukemia, or with the migration of hematopoietic or embryonic stem cells, said gene being controlled by a promoter that directs expression of said gene in Sca-1$^+$ cells. The transgenic non-human mammal provided by this invention possesses, as a result, a genotype that confers a greater tendency to develop human pathology of stem cell origin when compared to the non-transgenic mammal. Said non-human mammal is useful for studying said pathology among other goals and for evaluating potentially useful compounds for treating and/or preventing said pathology.

The expression "non-human mammal", as is used in this description, includes any non-human animal belonging to the class of mammals, for example, mice.

In a particular embodiment, the non-human transgenic animal provided by the invention is a transgenic mouse identified as:

Sca-1$^+$ BCR-ABL$^{P210}$: these mice develop chronic myeloid leukemia;

Sca-1$^+$ BCR-ABL$^{P190}$: these mice develop B-cell acute lymphoblastic leukemia;

Sca-1$^+$ Slug: these mice mobilise hematopoietic stem cells;

Sca-1$^+$ Snail: these mice mobilise embryonic stem cells;

Sca-1$^+$ HOX11: these mice develop T-cell acute lymphoblastic leukemia;

Sca-1$^+$ RHOM2/LMO-2: these mice develop T-cell acute lymphoblastic leukemias; and Sca-1$^+$ TAL1: these mice develop B-cell acute lymphoblastic leukemias For the generation of the transgenic non-human mammal provided by this invention, the DNA construct of the invention has been introduced into said mammal, or into a predecessor thereof, in an embryonic state, for example, in the state of a cell, or fertilized oocyte and, generally, not later than the g cell state.

Therefore, the invention provides a procedure for the preparation of a transgenic non-human mammal that possesses a chromosomal anomaly associated with a human pathology of stem cell origin, that comprises (i) introducing a DNA construct of the invention into a fertilized oocyte of a non-human transgenic mammal;
(ii) implanting said fertilized oocyte into a pseudopregnant wet nursing mother to produce descendants; and
(iii) analysing said descendants to evaluate the existence of activated genes and/or genes created by a chromosomal anomaly associated with a human pathology of stem cell origin.

In a particular embodiment, said chromosomal anomaly associated with a human pathology of stem cell origin is a human pathology selected from among the chromosomal anomalies associated with chronic myeloid leukemia, acute B-cell myeloid leukemia, T-cell acute lymphoblastic leukemia, or with migration of hematopoietic or embryonic stem cells (for example, alteration of the receptor c-kit or its ligand (SCF)), in which case, the descendents are analysed to evaluate the existence of activated genes and/or genes created by the chromosomal anomaly associated with the human pathology of stem cell origin in question.

There are different means conceived in the state of the art by which a sequence of nucleic acid can be introduced into an embryo of an animal such that it can be incorporated chromosomally in an active state, all of which can be applied to the generation of transgenic non-human mammals of the present invention. A method consists of transfecting the embryo with said sequence of nucleic acid as occurs naturally, and selecting the transgenic animals in which said sequence has been integrated onto the chromosome at a locus that gives as a result the activation of said sequence. Another method implies modification of the nucleic acid sequence, or its control sequences, before introducing it into the embryo. Another method consists of transfecting the embryo using a vector that contains the nucleic acid sequence to be introduced.

In a particular embodiment, the introduction of the DNA construct of the invention in the germ line of a non-human mammal is performed by means of microinjection of a linear DNA fragment that comprises the activatable gene operatively bound to the promoter that directs the expression in Sca-1$^+$ cells in fertilized oocytes of non-human mammals.

The fertilized oocytes can be isolated by conventional methods, for example, provoking the ovulation of the female, either in response to copulation with a male or by induction by treatment with the luteinising hormone. In general, a superovulation is induced in the females by hormonal action and they are crossed with males. After an appropriate period of time, the females are sacrificed to isolate the fertilized oocytes from their oviducts, which are kept in an appropriate culture medium. The fertilized oocytes can be recognised under the microscope by the presence of pronuclei. The microinjection of the linear DNA fragment is performed, advantageously, in the male pronucleus.

After the introduction of the linear DNA fragment that comprises the DNA construct of the invention in fertilized oocytes, they are incubated in vitro for an appropriate period of time or else they are reimplanted in pseudopregnant wet nursing mothers (obtained by making female copulate with sterile males). The implantation is performed by conventional methods, for example, anaesthetising the females and surgically inserting a sufficient number of embryos, for example, 10-20 embryos, in the oviducts of the pseudopregnant wet nursing mothers. Once gestation is over, some embryos will conclude the gestation and give rise to non-human transgenic mammals, which theoretically should carry the DNA construct of the invention integrated into their genome and present in all the cells of the organism. This progeny is the G0 generation and their individuals are the "transgenic founders". The confirmation that an individual has incorporated the injected nuclear acid and is transgenic is obtained by analysing the individuals of the progeny. To do this, from a sample of animal material, for example, from a small sample from the animal's tail (in the event that it is, for example, a mouse) or a blood example, the DNA is extracted from each individual and analysed by conventional methods, for example, by polymerase chain reaction (PCR) using the specific initiators or by Southern blot or Northern blot analysis using, for example, a probe that is complementary to, at least, a part of the transgene, or else by Western blot analysis using an antibody to the protein coded by the transgene. Other methods for evaluating the presence of the transgene include, without limitation, appropriate biochemical assays, such as enzymatic and/or immunological assays, histological staining for particular markers, enzymatic activities, etc.

In general, in transgenic animals, the inserted transgene is transmitted as a Mendelian characteristic and so it is not difficult to establish the stable lines of each individual. If the G0 individuals are crossed with the parent strain (retrocrossing) and the transgene behaves with Mendelian characteristics, 50% of the progeny will be heterozygotic for the inserted transgene (hemizygotic). These individuals constitute the G1 progeny and a transgenic line that can be maintained indefinitely, crossing hemizygotics of the G1 generation with normal individuals. Alternatively, individuals of the G1 generation can be crossed among themselves to produce 25% homozygotics for the inserted transgene, 50% hemizygotics and 25% without the transgene provided the transgene does not affect the viability of the descendents.

The progeny of a non-human transgenic mammal provided by this invention, such as the progeny of a transgenic mouse provided by this invention can be obtained, therefore, by copulation of the transgenic animal with an appropriate individual, or by in vitro fertilization of eggs and/or sperm of the transgenic animals. As used in this description, the term "progeny" or "progeny of a non-human transgenic mammal" relates to all descendents of a previous generation of the non-human transgenic mammals originally transformed. The progeny can be analysed to detect the presence of the transgene by any of the aforementioned methods.

The invention also relates to a non-human transgenic mammal cell line that contains a DNA construct of the invention on its genome, that is to say, a construct that comprises a gene that is created and/or activated by a chromosomal anomaly associated with chronic myeloid leukemia, B-cell acute lymphoblastic leukemia, T-cell acute lymphoblastic leukemia, or the migration of hematopoietic or embryonic stem cells, said gene being under the control of a promoter that directs the expression of said gene in Sca-1$^+$ cells. In a particular embodiment, said cell line is a murine cell line.

In another aspect, the invention relates to the use of a promoter that directs the expression of a gene in Sca-1$^+$ cells for the generation of non-human animal models that reproduce the human neoplastic or non-neoplastic pathology, which has its origin in hematopoietic or non-hematopoietic stem cells, such as non-human animal models that present a chromosomal anomaly associated with a human pathology of stem cell origin, for example, a chromosomal anomaly associated with chronic myeloid leukemia, B-cell acute lymphoblastic leukemia, T-cell acute lymphoblastic leukemia, or the migration of hematopoietic or embryonic stem cells. In a particular embodiment, said promoter that directs expression of a gene in Sca-1$^+$ cells is a pLy-6E.1 promoter of mice.

The transgenic non-human mammal provided by this invention, its progeny or the cell line provided by this invention, are useful for, among other applications, evaluating potentially useful compounds for treating and/or preventing a chromosomal anomaly associated with neoplastic or non-neoplastic human pathology of either hematopoietic or non hematopoietic stem cell origin, for example, chromosomal anomalies associated with chronic myeloid leukemia, B-cell acute lymphoblastic leukemia T-cell acute lymphoblastic leukemia, or the migration of hematopoietic or embryonic stem cells. Therefore, the invention also refers to the use of said non-human transgenic mammal, its progeny or a cell line provided by this invention, in the evaluation of potentially useful compounds for the treatment and/or prevention of a chromosomal anomaly associated with human pathology of stem cell origin. In a particular embodiment, said chromosomal anomaly is selected from the chromosomal anomalies associated with chronic myeloid leukemia, B-cell acute lymphoblastic leukemia, T-cell acute lymphoblastic leukemia, or the migration of hematopoietic or embryonic stem cells.

In the case of transgenic animals, the evaluation of the potentially useful compound for the treatment and/or prevention of said human pathology of stem cell origin can be performed by administration of the compound to be tested to said transgenic animal, at different doses, and evaluating the physiological response of the animal over time. The administration of the compound to be assayed can be oral or parenteral, depending on the chemical nature of the compound to be evaluated. In some cases, it may be appropriate to administer the compound in question along with cofactors that enhance the effect of the compound.

In the case of cell lines of the invention, the evaluation of the potentially useful compound for the treatment and/or prevention of said human pathology of stem cell origin can be performed by adding the compound to be assayed to a cell culture medium for an appropriate period of time, at different concentrations, and evaluating the cellular response to the compound over time using appropriate biochemical and/or histological assays. At times, it may be necessary to add the compound in question to the cellular culture medium along with cofactors that enhance the effect of the compound.

In another aspect, the invention relates to the use of a promoter that directs the expression a gene in Sca-1$^+$ cells as a vehicle of therapeutic strategies for the treatment and/or prevention of a chromosomal anomaly associated with a human pathology of stem cell origin, for example in the treatment and/or prevention of a chromosomal alteration associated with a human pathology of stem cell origin selected from the chromosomal anomalies associated with chronic myeloid leukemia, B-cell acute lymphoblastic leukemia, T-cell acute lymphoblastic leukemia, or the migration of hematopoietic or embryonic stem cells. The fact that the promoter directs the expression of a transgene in Sca-1$^+$ cells such as stem cells allows the specific and exclusive expression of different therapeutic strategies in stem cells. In a particular embodiment, said promoter that directs expression of a gene in Sca-1$^+$ genes is the pLy-6E.1 promoter of mouse.

Among the therapeutic strategies for the treatment and/or prevention of chromosomal anomalies associated with human pathologies of stem cell origin developed by means of the use of a promoter that directs the expression of a gene in Sca-1$^+$ cells as a vehicle for said therapeutic strategies is the deactivation of a malign gene or fusion gene, for example, in neoplasias, or else the inclusion of a functional gene that is lacking or the replacement of a defective gene with a functional gene, for example, in immunodeficiencies. These therapeutic strategies may materialise through (i) the preparation of a DNA construct that comprises said promoter that directs the expression of a gene in Sca-1$^+$ cells and a therapeutic gene appropriate for the treatment and/or prevention of the chromosomal anomaly association with the human pathology of stem cell origin to be treated and/or prevented, said therapeutic gene being under the control of said gene that directs the expression in Sca-1$^+$ cells; and (ii) the incorporation of said DNA construct in a vector or system that helps in the process of exogenous gene transfer to a cell, facilitating the intracellular delivery and bioavailability thereof such that this gene can function correctly. By way of illustration, said vectors or systems can be viral vectors, for example, based on adenovirus, lentivirus, retrovirus, etc, or non-viral such as DNA-liposome, DNA-polymer, DNA-polymerliposome complexes, etc [see "Nonviral Vectors for Gene Therapy", edited by Huang, Hung and Wagner, Academic Press (1999)].

As used in this description, the term "gene therapy" refers to a gene or a gene construct useful for the treatment and/or prevention of a chromosomal anomaly associated with human pathology of stem cell origin, and includes ribosomes, genes, fusions or anti-sense gene constructs, and, in general, any gene, gene fusion or gene construct useful against the gene created and/or activated by the anomalous chromosome in question, for example, chronic myeloid leukemia, B-cell acute lymphoblastic leukemia, T-cell acute lymphoblastic leukemia, alterations in the c-kit receptor or its ligand (SCF), etc.

The invention relates, in addition, to a pharmaceutical composition that comprises a DNA construct that comprises a suitable therapeutic gene for the treatment and/or prevention of a chromosomal anomaly associated with a human pathology of stem cell origin to be treated and/or prevented, and a promoter that directs the expression of a gene in Sca-1$^+$ cells, said gene being under the control of said promoter that directs the expression in Sca-1$^+$ cells, along with, optionally, one or more pharmaceutically acceptable excipients. Said DNA construct that comprises the promoter and the therapeutic gene can be obtained by conventional techniques in genetic engineering. The excipients that can be present in the pharmaceutical composition of the invention will depend on, among other things, the route of administration of said pharmaceutical composition. A review of the different routes of administration of active substances, of the excipients to be used, and their manufacturing procedures can be found in the *Tradado de Farmacia Galénica* C. Fauli i Trillo, Luzán 5, S.A. de Ediciones, 1993.

In a particular embodiment, due to the nature of the gene of the active ingredient (DNA construct) of the pharmaceutical composition of the invention, this comprises vectors or systems that help in the process of exogenous gene transfer to a cell which contains said DNA construct in its interior, which can be viral, for example, based on the adenovirus, lentivirus, retrovirus, etc., or non-viral such as the DNA-liposome, DNA-polymer, DNA-polymer-liposome complexes, etc. [see "Nonviral Vectors for Gene Therapy", edited by Huang, Hung and Wagner, Academic Press (1999)].

The invention also relates to the use of a promoter that directs the expression of a gene in Sca-1$^+$ cells in the elaboration of a pharmaceutical composition for the treatment and/or prevention of an anomalous chromosome associated with human pathology of stem cell origin, for example, chronic myeloid leukemia, B-cell acute lymphoblastic leukemia, T-cell acute lymphoblastic leukemia, or the migration of hematopoietic or embryonic stem cells (for example, alterations in the c-kit receptor or its ligand).

The following examples illustrate the invention and should not be considered limiting the scope thereof. Example 1 describes the generation of transgenic mice, while Example 2 shows the use of said transgenic mice as models for in vivo study of human pathologies of stem cell origin. To do this, the characteristic chromosomal translocations have been selected that lead to gene fusions that code for chimeric proteins associated with human leukemias (see Example 2). The altered expression of said gene fusions has been implicated in a characteristic subgroup of human leukemias. Transgenes have been introduced containing said gene fusions in mouse genomes in which the expression of said transgenes is directed satisfactorily by the mouse promoter pLy-6E.1 in Sca-1$^+$. The resulting overexpression of said gene products gives rise to most of the symptoms of human leukemias studied in each case, including the presence of blasts (if appropriate) and a concordant block in the differentiation programme. No tumors from other tissues have been found in transgenic mice, which leads to the conclusion that the overexpression of said transgenes is a key factor in the human leukemias studied, thus providing the first murine model that mimics in vivo human pathology with which the associated gene fusions studied are associated. These results show that the transgenic mice provided by this invention constitute a new model for studying in vivo the biology of the transgenes studied and indicate the effectiveness of this strategy for studying the role of specific chromosomal anomalies in the development of tumors.

EXAMPLES

The Materials and Methods used in the Examples that are described below were as follows.

Materials

Promoter: The promoter pLy-6E.1 was used for directing the tissue specific expression of the different transgenes (cDNA) in C57BL76 mice (Jackson Laboratory). This promoter is well characterised and the fragment of 16 kilobases (kb) used contains all the elements necessary for the selective expression in Sca-1$^+$ cells [Miles C, Sanchez M-J, Sinclair A, and Dzierzak, E (1997). "Expression of the Ly-6E.1 (Sca-1) transgene in adult hematopoietic stem cells and the developing mouse embryo"; Development 124, 537-547].

Genes: The genes used were the following:

Human BCR-ABL$^{P210}$, gene fusion that is produced as a consequence of the t(9:22)(q34:q11) and it is associated with chronic myeloid leukemia; patients who present this chromosomal anomaly develop blast crisis over time, which is a characteristic phenomenon of said disease course;

Human BCR-ABL$^{P190}$, an oncogene generated by chromosomal translocation t(9:22) and associated with B-cell acute lymphoblastic leukemia;

Murine Slug, a gene that participates in the mobilisation of hematopoietic stem cells;

Murine Snail, a gene of the Slug family that participates in embryonic stem cell migration;

Human HOX11, a gene activated by anomalous chromosomes associated with T-cell acute lymphoblastic leukemias;

Human RHOM2/LMO-2, a gene activated by chromosomal anomalies associated with T-cell acute lymphoblastic leukemias; and Murine TAL1, a gene activated by anomalous chromosomes associated with T-cell acute lymphoblastic leukemias.

The activatable genes identified as BCR-ABL$^{P210}$, BCR-ABL$^{P190}$, HOX11, RHOM2/LMO-2 and TAL1 are described in Annu Rev. Genet. (1997) 31: 429-453; the Slug gene is described in Science (1994) 264:835-849; and the Snail gene is described in Developmental Biology (1998) 198: 277-285; Development (1998) 125:3111-3121; and Gene (2000) 257: 1-12.

Mice: The mice used are C57BL/6×CBA and the wet nursing mothers are CD1. These animals are available commercially, for example, from the Jackson Laboratory (US).

Methods

Generation and Selection (Screening) of Transgenic Mice

The different cDNA (human BCR-ABL$^{P190}$, human BCR-ABL$^{P210}$, murine Slug, murine Snail, HOX11, human LMO2/RHOM2 and murine TAL1) were cloned at the ClaI site of the pLy-6E.1 promoter. The different cDNA were obtained by digestion with appropriate restriction endonucleases and each cDNA was cloned in the vector that contained the promoter pLy-6E.1 digested with ClaI by means of conventional techniques [Molecular Cloning, third edition, CSHL Press by Sambrook and Russell, 2001].

For the generation of transgenic mice Sca-1$^+$ BCR-ABL$^{P210}$, Sca-1$^+$ BCR-ABL$^{P190}$, Sca-1$^+$ Slug, Sca-1$^+$ Snail and Sca-1$^+$ RHOM2/LMO-2, a linear DNA fragment was obtained for microinjection by means of digestion with NotI, while for the generation of transgenic mice Sca-1$^+$ HOX11 and Sca-1$^+$ TAL1, the fragment of linear DNA for microinjection was obtained by means of digestion with BamH1. The different linear DNA fragments were microinjected into fertilized C57BL/6J×CBA mouse oocytes. The founding transgenic mice were identified by means of Southern blot analysis using specific probes that recognised said cDNA in samples of DNA extracted from the mice's tails.

The preparation of fertilized oocytes, the microinjection of the DNA constructs containing the promoter and the operatively linked activatable gene, the reimplantation of the fertilized oocytes into which said DNA constructs had been injected into the pseudopregnant wet nursing mothers and the maintenance of the wet nursing mothers during gestation were performed by means of the use of conventional techniques [Hogan, Constantini & Lacy (1986) "Manipulating the Mouse Embryo. A Laboratory Manual", Cold Spring Harbor Laboratory, Cold Spring Harbor (1986)]. The percentages of (i) fertilized oocytes that were transformed correctly and (ii) embryos that developed to termination and gave rise to transgenic mice were similar to those described by Hogan, Constantini & Lacy (1986), cited above.

The progeny/descendents of the transgenic mice were obtained by crossing the founding mouse with C57BL/6× CBA mice and identifying positive mice by Southern blot analysis with specific probes that recognised the cDNA.

Fetal Analysis

For the staining for cytometry, the following monoclonal anti-mouse antibodies conjugated to phycoerythrin (PE) (all from Pharmingen): CD45R/B220, Thy-1.1 and Thy-1.2, myeloid markers (Mac 1/CD11b and Gr-1) and Sig. Suspensions of cells from whole blood samples obtained by routine techniques were incubated with CD32/CD16 anti-mouse (Pharmingen) purified to block the binding to receptors by Fc and with an appropriate dilution of different antibodies at room temperature to 4° C., respectively. The erythrocytes were lysed using lysis solution (Becton Dickinson). The samples were washed twice with phosphate buffer saline (PBS) and resuspended in PBS. The dead cells present in the samples were excluded by means of staining with propidium iodide. The samples and the data were analysed in a FACScan using the CellQuest program (Becton Dickinson).

PCR Analysis mRNA was obtained from different tissues of chimeric mouse. By means of reverse transcription of each preparation of RNA treated with DNAse I (HT) of RNase, cDNA was obtained. The cDNA was submitted to PCR using the specific indicators in each case [the direct initiator (5') corresponded to the first 20 bases of cDNA and the inverse initiator (3') was complementary to the last 20 bases of the cDNA]. The reactions were performed following the instructions of the supplier of Taq polymerase (Perkin-Elmer Cetus) under the following conditions: 1 minute at 95° C., 1 minute at 55° C. and 1 minute at 72° C. for 25 cycles with a final elongation of 10 minutes at 72° C.

Histological Analysis

The tissue samples were fixed in formaldehyde at 4% in PBS and bathed in paraffin. Thin laminas were cut which were processed and stained with haematoxylin-eosin by means of routine techniques. The laminas were examined and photographed.

Western Blot Analysis

Suspensions of cells from the spleen were analysed by immunoblotting techniques using conventional methods [Antibodies: A laboratory manual. Harlow and Lane. CSH, 1988].

Immunoglobulin Regrouping/TCR Gene

DNA was prepared from different tissues by means of conventional techniques. The DNA was digested with BamHI and the Southern blots were analysed with a probe of a specific immunoglobulin [Blood (rapid publication) 90: 2168-2174 (1997)].

Cell Transfer

Cells from donor mouse organs were suspended, washed and injected intravenously into the tail of receptor mice (NOD/SCDI) (The Jackson Laboratory) aged 4-6 months. The mice were monitored once a week and were sacrificed for histopathological studies and collection of tissues for DNA analysis when they were moribund.

Example 1

Generation of Transgenic Mice 1.1 Generation of Sca-1$^+$ BCR-ABL$^{P210}$ Transgenic Mice In order to examine the direct consequences of the expression of the gene product BCR-ABL$^{P210}$ (gene fusion that results as a consequence of the t(9:22)(q34;q11) and that is associated with chronic myeloid leukemia) in vivo, the cDNA of the chimeric human protein BCR-ABL$^{P210}$ was cloned under the control of the promoter pLy-6E.1 of mouse and the fertilized oocytes were injected into C57BL/6J×CBA mice following the technique described previously in the section on the "Methods". Two transgenic founder mice (Sca-1$^+$ BCR-ABL$^{P210}$) showed a capacity to transmit the transgene down the germ cell line. The expression of the transgene was observed in both lines and the progeny multiplied up to level F7 (generation 7). The expression of the transgene was demonstrated by PCR and/or Western blot analysis. Both cell lines showed preferential expression in Sca-1$^+$ cells. The expression of the transgene was detected both in male and female mice, with similar findings in both lines of transgenic Sca-1$^+$ BCR-ABL$^{P210}$ mice.

1.2 Generation of other Transgenic Mice

Figure 3A:
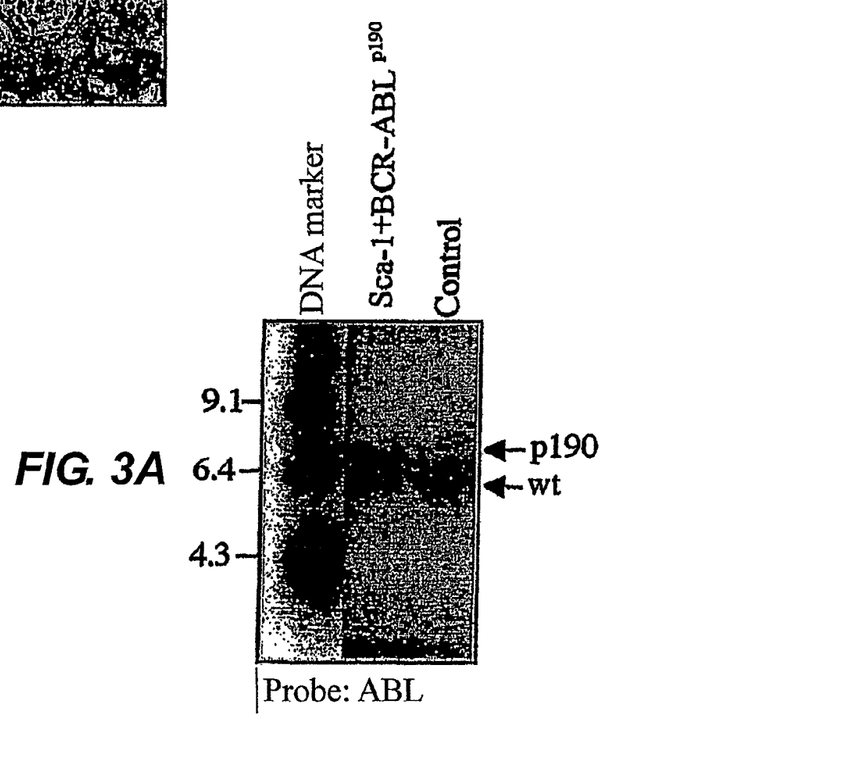
FIG. 3A shows DNA analysis by means of a Southern Blot of Sca-1+ BCR-ABLp190 mice and hybrid controls with an ABL specific probe. The presence of the transgene (p190) is observed in Sca-1+ BCR-ABL$^{p190}$ mice.
Figure 3B:
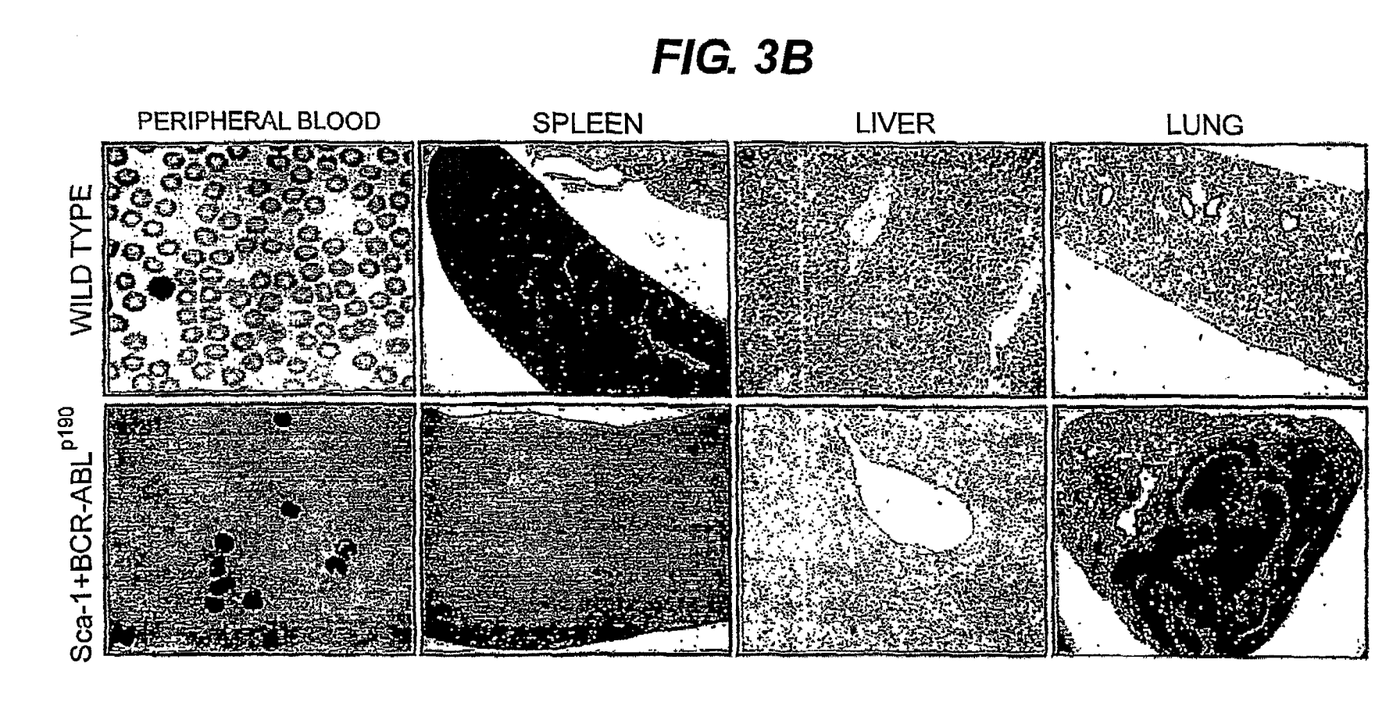
FIG. 3B shows the results from the representative histological examination of the spleen, liver, lungs and staining of the peripheral blood of control mice and Sca-1+ BCR-ABL$^{P190}$ mice. All histological sections are stained with haematoxylin and eosin and the peripheral blood staining with Giemsa and the presence of leukaemic cells in Sca-1+ BCR-ABL$^{P190}$ mice was observed.
Figure 3C:
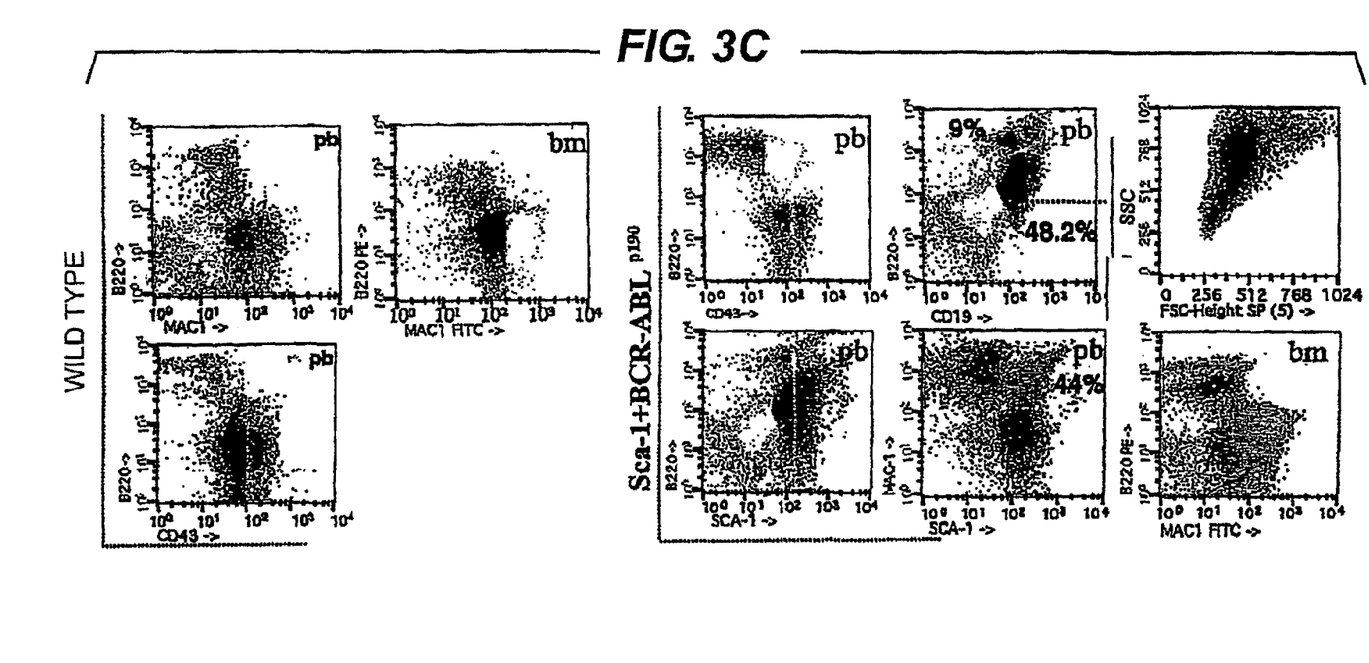
FIG. 3C shows the representative analysis of the cell composition present in bone marrow (BM) and peripheral blood (PB) of control mice and Sca-1+ BCR-ABL$^{p190}$ mice. Cells isolated from control mice and Sca-1+ BCR-ABL$^{p190}$ mice were stained with the indicated monoclonal antibodies [Mac1 for the myelomonocyte series; B220, CD19 and CD43 for the lymphoid series and Sca1 for the stem series] and they were analysed by flow cytometry. The percentage of neoplastic cells in Sca-1+ BCR-ABL$^{p190}$ mice is indicated. The distribution of neoplastic cells for B220/CD19 is shown in accordance with the size (size, SSC) and granularity (forward/FSC).

In order to examine the direct consequences of the expression of the gene products human BCR-ABL$^{P190}$, murine Slug, murine Snail, human HOX11, human RHOM2/LMO-2 and murine TAL1 in vivo the corresponding cDNA were cloned under the control of the promoter pLy-6E.1 of mouse and the resulting constructs, previously linearised, were injected into fertilized oocytes of C57BL/6J×CBA mice following the technique described previously in the section on the "Methods". Two transgenic founder mice were obtained for each construct that demonstrated their capacity to transmit the transgene down the germ cell line. Proceeding in this way, transgenic mice were obtained identified as:

Sca-1$^+$ BCR-ABL$^{P190}$ (they develop B-cell acute lymphoblastic leukemia) [see FIG. 3];

Sca-1$^+$ Slug (produce migration of hematopoietic stem cells but not leukemias);

Sca-1$^+$ Snail (produce migration of hematopoietic stem cells but not leukemias);

Sca-1$^+$ HOX11 (develop T-cell acute lymphoblastic leukemias);

Sca-1$^+$ RHOM2/LMO-2 (develop T-cell acute lymphoblastic leukemias); and

Sca-1$^+$ TAL1 (develop T-cell acute lymphoblastic leukemias).

In all cases, the expression of the transgene is observed in both lines and the progeny multiplies up to the F7 level (generation 7). The expression of the transgene was demonstrated by PCR and/or Western blot analysis. Both cell lines showed preferential expression in Sca-1$^+$ cells. The expression of the transgene was detected both in male mice and female mice, with similar findings in both lines of transgenic mice.

Example 2

Production of Leukemias in Transgenic Mice

Although in human pathology, the chimeric products of the genes Sca-1$^+$ BCR-ABL$^{P210}$, Sca-1$^+$ BCR-ABL$^{P190}$, Sca-1$^+$ Slug, Sca-1$^+$ Snail, Sca-1$^+$ HOX11, Sca-1$^+$ RHOM2/LMO-2 and Sca-1$^+$ TAL1 are associated with different types of leukemia, specifically, with chronic myeloid leukemia (BCR-ABL$^{P210}$), B-cell acute lymphoblastic leukemia (BCR-ABL$^{P190}$) and T-cell acute lymphoblastic leukemias (HOX11, RHOM2/LMO-2 and TAL1), the current murine models for said leukemias have failed when it comes to reproducing said pathologies consistently [Annu. Rev. Genetics (1997) 31:429-453; Current Genomics (2000), 1: 71-80] due to the difficulty of choosing a promoter for manipulating the expression of the appropriate cell type.

Figure 1A:
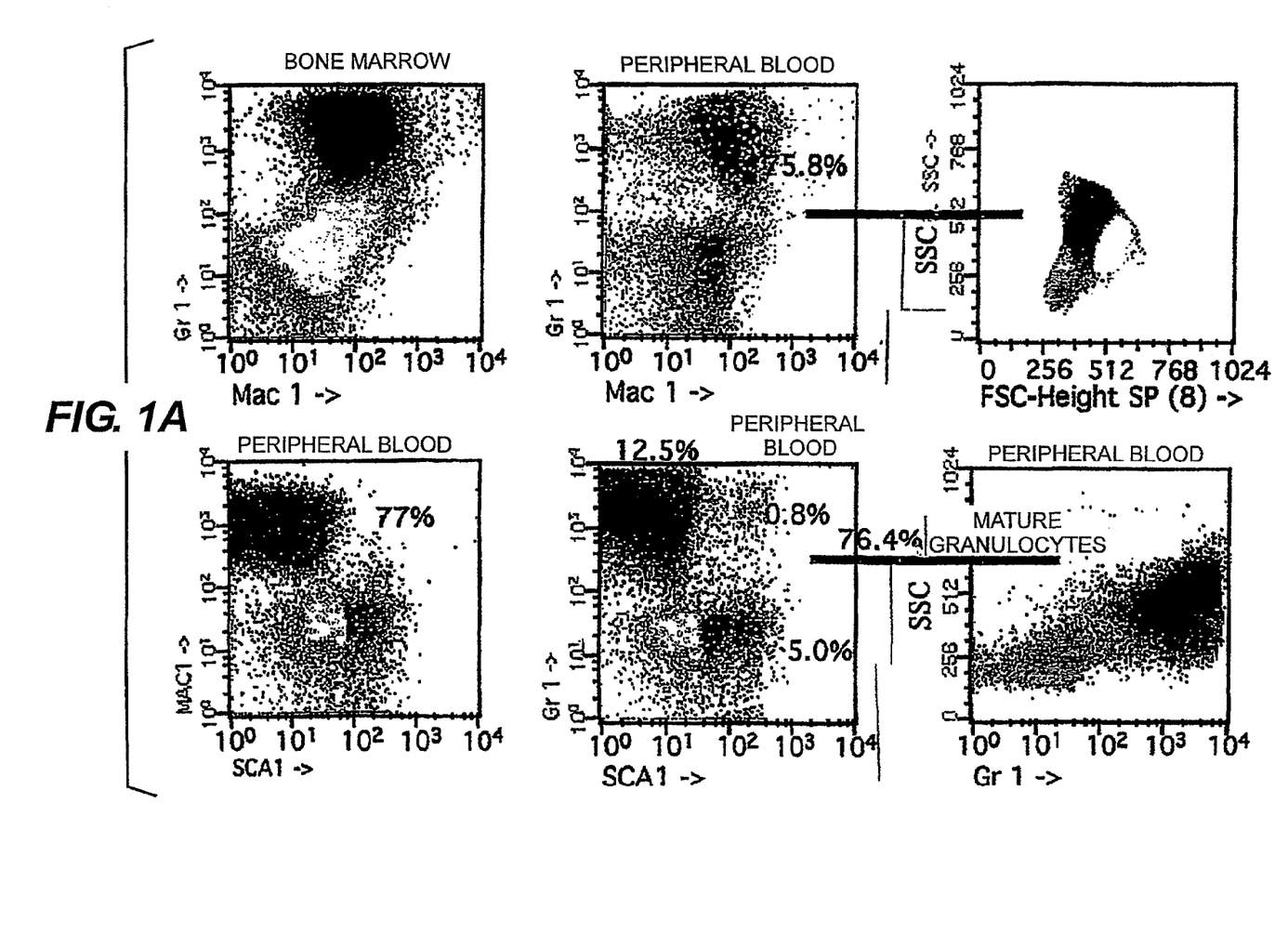
FIG. 1A shows the representative analysis of the cell composition present in the bone marrow (BM) and in the peripheral blood (PB) of BCR-ABLP$^{210}$ mice. Cells isolated from Sca-1+ BCR-ABLP$^{210}$ mice were stained with the indicated monoclonal antibodies [Gr-1, for the granulocyte series; Mac1 for the myelomonocyte series and Sca1 for the stem series] and they were analysed by flow cytometry. The percentage of positive cells is indicated. The distribution of cells positive for Gr-1+Mac1 and Gr-1+Sca1 is shown in accordance with size (size, SSC) and the granularity (forward, FSC).
Figure 1B:
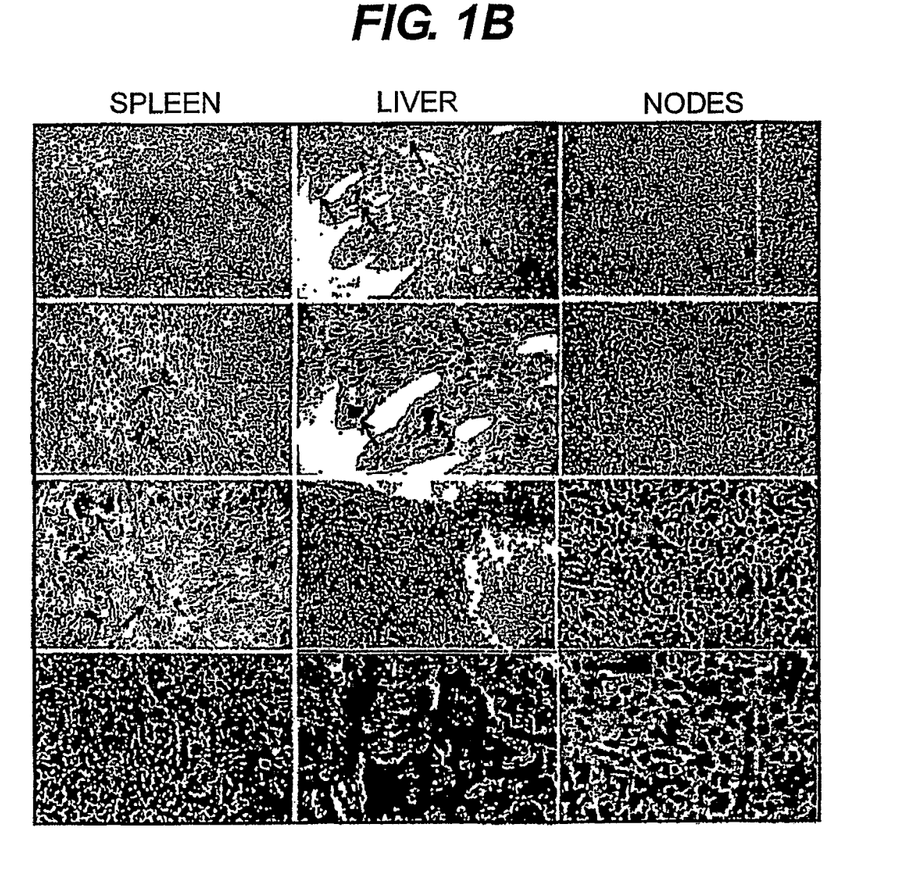
FIG. 1B shows the result of the representative histological examination of sections of spleen, liver and lymphatic nodules of Sca-1+ BCR-ABL$^{210}$ mice with chronic myeloid leukemia. All sections were stained with haematoxylin and eosin. The arrows indicate the present of fibrosis and megakaryocytes typical of the chronic myeloid leukemia process.
Figure 1C:
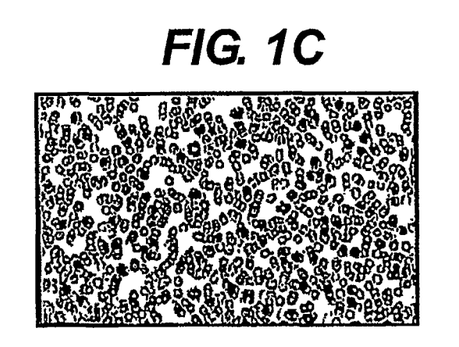
FIG. 1C shows a representative staining of the peripheral blood of Sca-1+ BCR-ABLP210 mice stained with Giemsa.
Figure 2A:
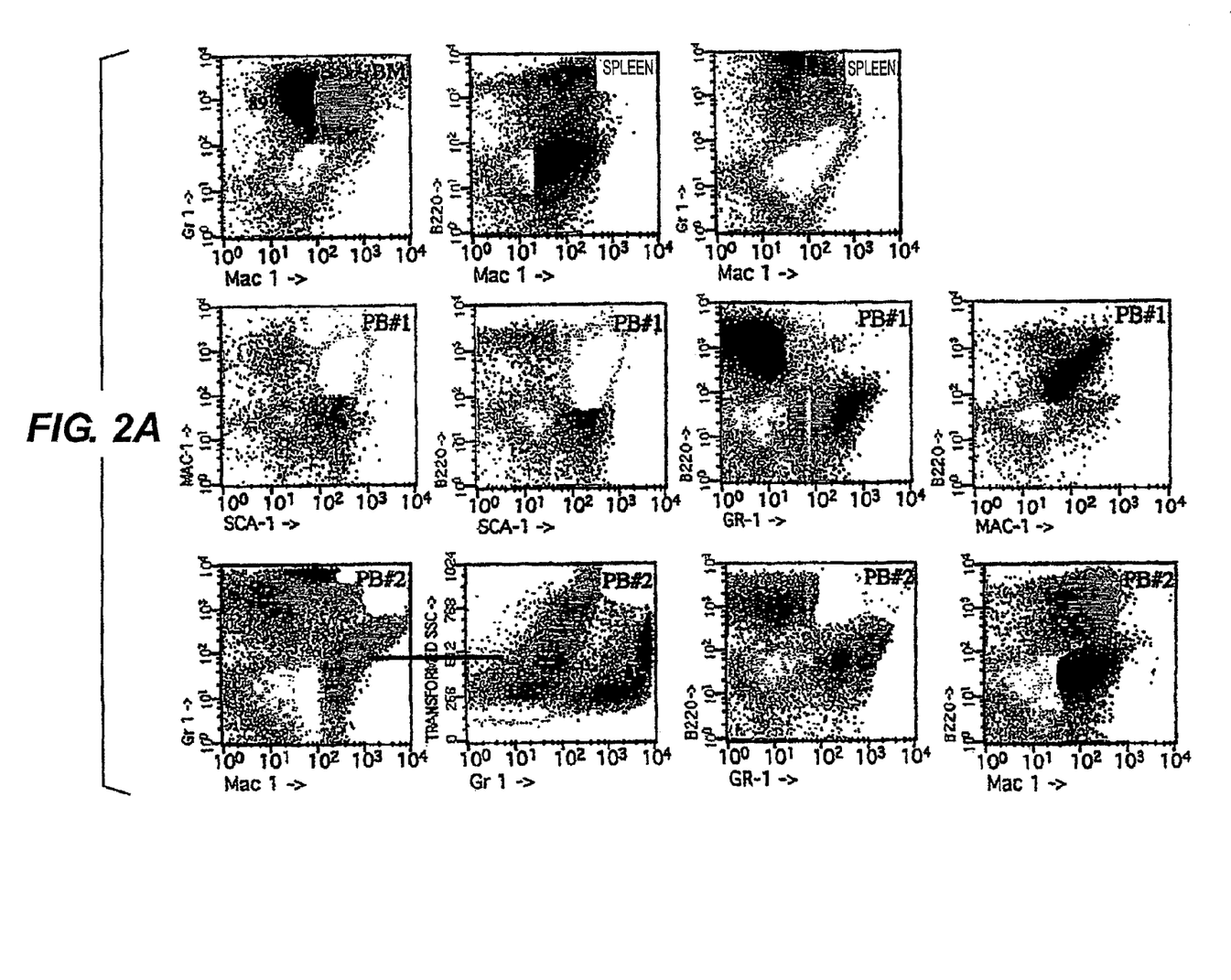
FIG. 2A shows the representative analysis of the cell composition present in the bone marrow (BM), spleen and in the peripheral blood (PB) of Sca-1+ BCR-ABLP$^{210}$ mice in blast crisis. Cells isolated from Sca-1+ BCR-ABLP$^{210}$ mice in blast crisis were stained with the indicated monoclonal antibodies [Gr-1, for the granulocyte series; Mac1 for the myelomonocyte series; B220 for the B lymphoid series and Sca1 for the stem series] and they were analysed by flow cytometry. An example of B lymphoid blast crisis (PB#1) is shown and another one in myeloid blast crisis (PB#2). The distribution of cells positive for Gr-1+Mac1 is shown in accordance with size (size, SSC).
Figure 2B:
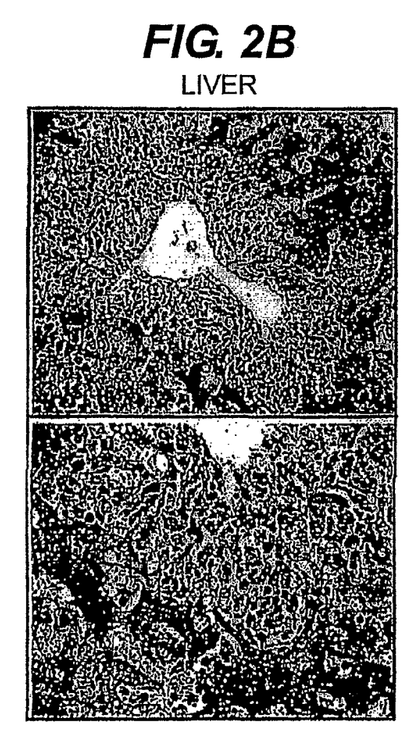
FIG. 2B shows the result of the representative histological examination of sections of liver of Sca-1+ BCR-ABLP$^{210}$ mice with blast crisis. All sections were stained with haematoxylin and eosin. Hepatic infiltration by leukemia cells was observed.
Figure 2C:
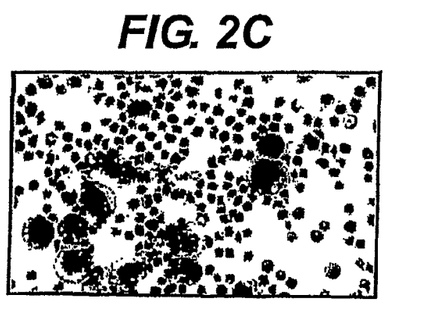
FIG. 2 consists of a set of plots and photographs that constitute the phenotype and histological demonstration of myeloid and lymphoid blast crisis in Sca-1+ BCR-ABLP$^{210}$ mice.

The detailed analysis of the leukemia cells of different transgenic mice tested (Sca-1$^+$ BCR-ABL$^{P210}$ (FIGS. 1 and 2), Sca-1$^+$ BCR-ABL$^{P190}$ (FIG. 3), Sca-1$^+$ HOX11, Sca-1$^+$ RHOM2/LMO-2 and Sca-1$^+$ TAL1) allowing diagnosis of the corresponding leukemias to be established. Staining with haematoxylin/eosin showed that leukemia cells have a lymphoid/myeloid morphology. Most of the mononuclear cells of peripheral blood have a phenotype compatible with the corresponding leukemias.

In order to test the tumorogenicity of the transgenic mice cells assayed, 1×10$^6$ cells were injected intravenously into normal non-irradiated NOD/SCID mice. All mice injected progressively developed leukemias within 6-11 weeks after transplant. On the contrary, none of the 20 mice injected with cells from 10 control mice developed a leukemia whose origin could be attributed to the donor. The transplanted cells developed the same class of leukemia. In addition, the origin of leukemia clones of donor mice were confirmed by means of a PCR analysis, revealing the presence of the corresponding transgenes.

More specifically, in each case, the male and female transgenic mice uniformly showed the same symptoms (of the corresponding pathology), starting after 8 weeks with the clinical signs increasing over the course of time until the death of 100% of the mice, which took place at 12-16 months. The founding mice were males and females and they developed clinical symptoms associated with the corresponding disease, in a similar way to that of the other transgenic mice. All transgenic mice died due to tumors aged 14-18 months. The percentage survival in the lines of the two founding mice was similar in each case. No tumors were observed in control groups consisting of an equal number mice in each non-transgenic litter. Often, the animals suffered tachypnoea and so were sacrificed. On performing the autopsy, it was observed that the animals had developed some palpable masses (unique for each pathology) which implicated hematopoietic tissue which, after dissection, showed organs from 5 to 100 times larger than normal organs. The infiltration of the tumor in non-hematopoietic tissues was visible and was confirmed by examination with a microscope. This examination is consistent with the hematopoietic tissue disease. However, tumors from other tissues were not observed in these transgenic mice. The histological analysis of these animals showed a marked infiltration of leukaemic cells from hematopoietic tissues (spleen and bone marrow) and non-hematopoietic tissues (liver, lung, testicles, etc.).

Therefore, the murine models studied not only resemble the regrouping that takes place in the human leukemias considered [chronic myeloid leukemia, B-cell acute lymphoblastic leukemias and T-cell acute lymphoblastic leukemias] but they also reproduce the same phenotype with which the implicated gene fusions are associated in human pathologies. These results validate these murine models as ideal models for the in vivo study of the biology of the transgenes assayed (BCR-ABL$^{P210}$, BCR-ABL$^{P190}$, Sca-1$^+$ HOX11, Sca-1$^+$ RHOM2/LMO-2 and Sca-1$^+$ TAL1).

Overall, the results obtained make manifest the generation of new mouse models in which the expression of the corresponding oncogenes is directed by regulating elements of control of the expression of the mouse promoter pLy-6E.1, recapitulating the consequences of the chromosomal anomaly.

The invention claimed is:

1. A method for evaluating a candidate compound for the treatment of chronic myeloid leukemia, the method comprising:
   (a) administering a candidate compound to a transgenic mouse whose genome comprises a DNA construct comprising a nucleic acid sequence encoding human BCR-ABL$^{P210}$ protein operably linked to a pLy-6E.1 promoter;
   wherein said transgenic mouse exhibits expression of human BCR-ABL$^{P210}$ specifically in Sca-1$^+$ cells and in the absence of said administering exhibits fibrosis of the spleen and blast crisis subsequent to said fibrosis; and
   (b) evaluating the effect of said candidate compound on development of fibrosis of the spleen and blast crisis subsequent to said fibrosis in said transgenic mouse.

2. A method for evaluating a candidate compound for the treatment of B-cell acute lymphoblastic leukemia, the method comprising:
   (a) administering a candidate compound to a transgenic mouse whose genome comprises a DNA construct comprising a nucleic acid sequence encoding human BCR-ABL$^{P190}$ protein operably linked to a pLy-6E.1 promoter;
   wherein said transgenic mouse exhibits expression of human BCR-ABL$^{P190}$ specifically in Sca-1$^+$ cells and in the absence of said administering exhibits co-expression of markers Mac 1 and B220 in bone marrow cells; and
   (b) evaluating the effect of said candidate compound on co-expression of markers Mac1 and B220 by bone marrow cells of said transgenic mouse.

3. A method for evaluating a candidate compound for the prevention of chronic myeloid leukemia, the method comprising:
   (a) administering a candidate compound to a transgenic mouse whose genome comprises a DNA construct comprising a nucleic acid sequence encoding human BCR-ABL$_{p210}$ protein operably linked to a pLy-6E.1 promoter;
   wherein said transgenic mouse exhibits expression of human BCR-ABL$^{P210}$ specifically in Sca-1$^+$ cells and in the absence of said administering develops fibrosis of the spleen and blast crisis subsequent to said fibrosis; and
   (b) evaluating the effect of said candidate compound on development of fibrosis of the spleen and blast crisis subsequent to said fibrosis in said transgenic mouse.

4. A method for evaluating a candidate compound for the prevention of B-cell acute lymphoblastic leukemia, the method comprising:
   (a) administering a candidate compound to a transgenic mouse whose genome comprises a DNA construct comprising a nucleic acid sequence encoding human BCR-ABL$^{P190}$ protein operably linked to a pLy-6E.1 promoter;
   wherein said transgenic mouse exhibits expression of human BCR-ABL$^{P190}$ specifically in Sca-1$^+$ cells and in the absence of said administering develops co-expression of markers Mac 1 and B220 in bone marrow cells; and
   (b) evaluating the effect of said candidate compound on co-expression of markers Mac1 and B220 by bone marrow cells of said transgenic mouse.

* * * * *